United States Patent
Lee

(10) Patent No.: US 12,139,156 B2
(45) Date of Patent: Nov. 12, 2024

(54) MULTIPURPOSE ELECTRIC VEHICLE CONTROL SYSTEM

(71) Applicant: Alpha Motor Corporation, Irvine, CA (US)

(72) Inventor: Kevin Kyung-Ho Lee, Irvine, CA (US)

(73) Assignee: Alpha Motor Corporation, Irvine, CA (US)

( * ) Notice: Subject to any disclaimer, the term of this patent is extended or adjusted under 35 U.S.C. 154(b) by 32 days.

(21) Appl. No.: 17/120,615

(22) Filed: Dec. 14, 2020

(65) Prior Publication Data
US 2024/0239360 A1    Jul. 18, 2024

(51) Int. Cl.
| | |
|---|---|
| *B60W 50/08* | (2020.01) |
| *A61L 2/00* | (2006.01) |
| *B60W 10/22* | (2006.01) |
| *B60W 50/00* | (2006.01) |
| *B62D 63/02* | (2006.01) |
| *G07C 5/00* | (2006.01) |
| *G07C 5/08* | (2006.01) |

(52) U.S. Cl.
CPC ............ *B60W 50/085* (2013.01); *A61L 2/00* (2013.01); *B60W 10/22* (2013.01); *B60W 50/0098* (2013.01); *B62D 63/025* (2013.01); *G07C 5/008* (2013.01); *G07C 5/0841* (2013.01); *B60W 2050/0064* (2013.01); *B60W 2510/222* (2013.01)

(58) Field of Classification Search
None
See application file for complete search history.

(56) References Cited

U.S. PATENT DOCUMENTS

| | | | |
|---|---|---|---|
| 2011/0291444 A1* | 12/2011 | Ische | B60P 3/42 296/193.04 |
| 2016/0129958 A1* | 5/2016 | Byrnes | B62D 63/025 180/12 |
| 2017/0197678 A1* | 7/2017 | Scaringe | B60K 1/00 |
| 2017/0274790 A1* | 9/2017 | Kim | B60L 1/00 |
| 2018/0186274 A1* | 7/2018 | Gurin | B62D 39/00 |
| 2018/0345971 A1* | 12/2018 | Birnschein | B62D 21/11 |

(Continued)

*Primary Examiner* — Christian Chace
*Assistant Examiner* — Shayne M. Gilbertson
(74) *Attorney, Agent, or Firm* — AVEK IP, LLC

(57) ABSTRACT

A multipurpose electric vehicle control system provides an electric vehicle made up of multiple detachably attached modules that can be interchanged to create different operational modes, and a control unit and a software that direct reconfigurations to vehicle subsystems, so as to selectively form different operational modes. The software also manages vehicle-related data. Exemplary reconfigurations to the structural configuration of vehicle subsystems include: performance settings, suspension adjustments, panel management, brake settings, transmission settings, security settings, battery management, power management, and entertainment settings. By making these reconfigurations to vehicle subsystems the electric vehicle selectively operates between a personal transport vehicle mode, a fleet service vehicle mode, and a commercial vehicle mode. The software also manages vehicle-related data, including: vehicle insurance, vehicle maintenance schedule, and vehicle service logs. A personal communication device, such as a smart phone, can control the software through a software application.

19 Claims, 7 Drawing Sheets

(56) References Cited

U.S. PATENT DOCUMENTS

| | | | |
|---|---|---|---|
| 2020/0369334 A1* | 11/2020 | Lee .......................... | B60K 1/04 |
| 2021/0080974 A1* | 3/2021 | Mackin .................... | B64F 1/32 |
| 2021/0101613 A1* | 4/2021 | Claesson ................. | B60P 3/423 |
| 2022/0009471 A1* | 1/2022 | Sjödin et al. ......... | B60W 30/18 |
| 2023/0166798 A1* | 6/2023 | Foran ..................... | C09J 175/04 |
| | | | 296/181.1 |

* cited by examiner

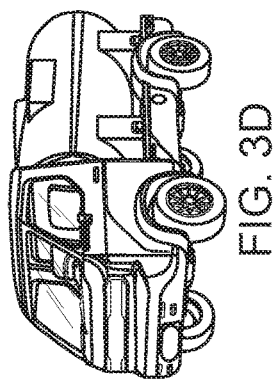
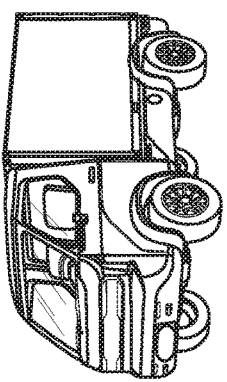
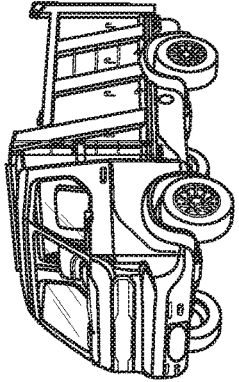
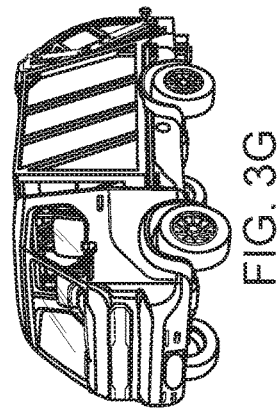
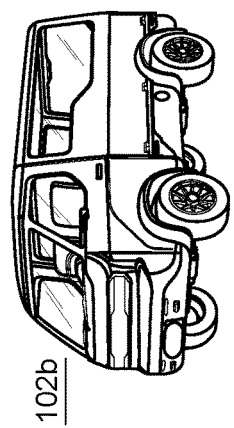
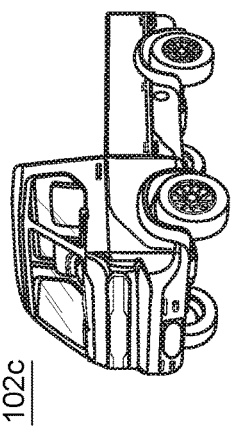
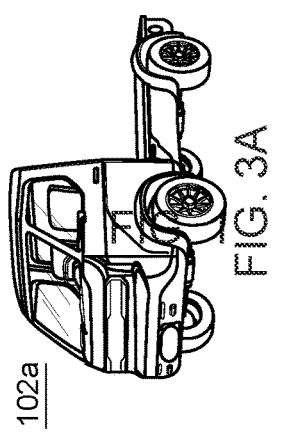
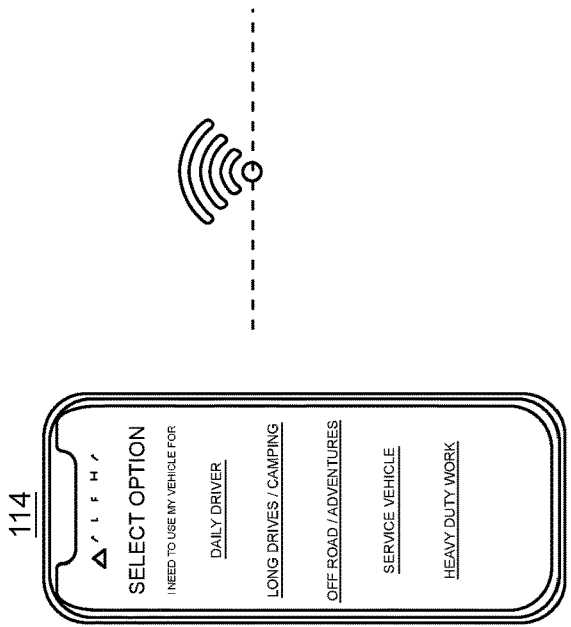

MULTIPURPOSE ELECTRIC VEHICLE CONTROL SYSTEM

FIELD OF THE INVENTION

The present invention relates generally to a multipurpose electric vehicle control system. More so, the present invention relates to an electric vehicle made up of multiple detachably attached modules that can be interchanged to create different operational modes, and a control system that provides an electric vehicle, which has integrated within, a control unit and a software that direct reconfigurations to the vehicle subsystems, so as to selectively form different operational modes; such that the electric vehicle can selectively operate between a personal transport vehicle mode, a fleet service vehicle mode, and a commercial vehicle mode; and further, the software manages vehicle-related data.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Generally, vehicle control systems help control operation of various subsystems of a vehicle, so that the vehicle can operate in different configuration modes for different conditions. For example, automatic transmissions can be controlled in sport, winter, economy and manual configuration modes in which the changes between gear ratios and other subsystem control parameters are modified so as to suit the prevailing conditions. Air suspensions are known with on-road and off-road configuration modes. Stability control systems can be operated at reduced activity so as to give the driver more direct control over the operation of the vehicle. Vehicle transmissions can be switched to provide drive to different numbers of wheels.

It is known in the art that electric vehicles utilize electrical energy as a source of power. This electrical means can be a substitute for the vehicles using fossil fuels. Generally, electric vehicles are required to be equipped with batteries having a large capacity in order to propel the vehicle through large distances. The batteries of such vehicles are required to be charged periodically, which can be a cumbersome task.

Generally, an electric vehicle operates with an electric motor drive as well as a rechargeable battery system. The vehicle is operated using power stored within the batteries, and when the batteries require, they can be recharged. It is known in the art that many consumers are motivated to purchase or drive an electric vehicle as an environmental choice, so as to minimize vehicle emissions.

Other proposals have involved multi-mode vehicles. The problem with these electric vehicles is that they do not have the capacity to convert into different operational modes by both the structural modular components, such as a rear operational module; and the reconfiguration of vehicle subsystems, such as the suspension, wheels, battery, electric motor, and interchangeable panels. Even though the above cited modular electric vehicles meet some of the needs of the market, a multipurpose electric vehicle control system. More so, the present invention relates to an electric vehicle made up of multiple detachably attached modules that can be interchanged to create different operational modes, and a control system that provides an electric vehicle, which has integrated within, a control unit and a software that direct reconfigurations to the vehicle subsystems, so as to selectively form different operational modes; such that the electric vehicle can selectively operate between a personal transport vehicle mode, a fleet service vehicle mode, and a commercial vehicle mode; and further, the software manages vehicle-related data, is still desired.

SUMMARY

Illustrative embodiments of the disclosure are generally directed to a multipurpose electric vehicle control system. The electric vehicle control system provides an electric vehicle made up of multiple detachably attached modules, that has integrated within, a control unit and a software that direct reconfigurations to the vehicle subsystems so as to selectively form different operational modes. For example, the suspension subsystem can be reconfigured to have harder or softer suspension springs. Other exemplary reconfigurations to the structural configuration of the vehicle subsystems may include, without limitation, performance settings, suspension adjustments, panel and window management, brake settings, transmission settings, security settings, battery management, power management, climate settings, and entertainment settings. By making these reconfigurations to the vehicle subsystems the electric vehicle can selectively operate between different operational modes, including: a personal transport vehicle mode, a fleet service vehicle mode, and a commercial vehicle mode. This unique capacity to reconfigure vehicle modes enables the vehicle operator to drive in multiple environments and operational modes. The software also serves to manage vehicle-related data, including: a vehicle insurance, a vehicle maintenance schedule, and a vehicle service log. A personal communication device, such as a smart phone, may be utilized to control the software through a software application.

In one aspect, a multipurpose electric vehicle control system, comprises:

an electric vehicle comprising a plurality of vehicle subsystems, the vehicle subsystems being operable in a plurality of operational modes, the vehicle subsystems including:
  a chassis module having a suspension subsystem, a wheel subsystem operatively connected to the suspension device, an electric motor subsystem operatively connected to the wheel subsystem for rotatably driving the wheel subsystem, a rechargeable battery subsystem operatively connected to the electric motor subsystem for charging the electric motor subsystem, and a transmission subsystem operatively joined with the electric motor subsystem and the wheel subsystem for transmitting power from the electric motor subsystem to the wheel subsystem;
  a body module being detachably attachable to the chassis module, the body module comprising an interchangeable panel subsystem; and
  one or more rear operational modules being interchangeably and detachably attached to the body module, whereby any combination of the rear operational modules attaches to the body module;
a control unit operable to reconfigure the structural configuration of the vehicle subsystems, whereby changing the structural configuration of the vehicle subsystems causes the operational modes to be reconfigured; and
a machine-readable storage medium containing machine-executable instructions operable to instruct the control unit to reconfigure the structural configuration of the vehicle subsystems, the machine-executable instructions further being operable to manage vehicle-related data.

In another aspect, the operational modes comprise a personal transport vehicle mode.

In another aspect, the operational modes comprise a fleet service vehicle mode.

In another aspect, the operational modes comprise a commercial vehicle mode.

In another aspect, the vehicle-related data management includes at least one of the following: a vehicle insurance, a vehicle maintenance schedule, and a vehicle service log.

In another aspect, the reconfigurations to the structural configuration of the vehicle subsystems include, at least one of the following: performance settings, suspension adjustments, panel and window management, brake settings, transmission settings, security settings, battery management, power management, climate settings, entertainment settings.

In another aspect, the control unit comprises a processor.

In another aspect, the machine-executable instructions operate remotely.

In another aspect, the machine-executable instructions operate remotely from a mobile communication device.

In another aspect, the suspension subsystem is operable to maintain a vertical load on the wheels, the suspension subsystem being detachably attachable to the chassis module.

In another aspect, the interchangeable panel subsystem comprises one or more front panels detachably attached to a front end of the body module.

In another aspect, the interchangeable panel subsystem comprises one or more rear panels detachably attached to a rear end of the body module.

In another aspect, the front and rear panels are operational to illuminate.

In another aspect, the front and rear panels form openings to enable passage of light.

In another aspect, the interchangeable panel subsystem comprises one or more side panels detachably attached to a left side and a right side of the body module.

In another aspect, the interchangeable panel subsystem comprises one or more roof panels detachably attached to a top end of the body module.

In another aspect, the rechargeable battery subsystem comprises a lithium ion battery pack.

In another aspect, the body module is defined by an interior space.

In another aspect, the interior space contains one or more interior components.

In another aspect, the interior components include at least one of the following: a cushion, a display screen, a sound system, a central air system, and a trim.

In another aspect, the transmission subsystem comprises a single-speed transmission assembly.

In another aspect, the suspension subsystem includes at least one of the following: struts, shock absorbers, and springs.

In another aspect, the control system also includes an air purification subsystem.

In another aspect, the control system also includes sterilization through UV interior lighting.

In another aspect, the control system also includes a temperature control subsystem.

In another aspect, the control system also includes a self-cleaning function.

In another aspect, the control system also includes a diagnostic subsystem that indicates exterior components that require replacement.

In another aspect, the control system also includes a diagnostic subsystem that indicates interior components that require replacement.

In another aspect, the control system also includes a diagnostic subsystem that indicates battery and motor components that require replacement.

One objective of the present invention is to selectively reconfigure the operational modes of an electric vehicle between a personal use mode and a service fleet mode.

Another objective is to provide software that adjusts the vehicle capabilities such as performance, suspension, security, battery management, power management, data management amongst various other settings.

Another objective is to provide an all-purpose electric vehicle that is designed for use in various environments, and have replaceable and interchangeable components.

Another objective is to provide a vehicle that offers multiple modes of use easily interchanged, including a personal transport vehicle mode, a service vehicle mode, and a commercial vehicle mode.

Another objective is to provide recyclable components, and rechargeable batteries.

Yet another objective is to provide a chassis module that has adjustable dimensions.

An exemplary objective is to provide interchangeable panels, including lights, for the body module.

Additional objectives are to enable power supplies, such as rechargeable batteries and hydrogen tanks, to be easily interchanged to the chassis module.

Additional objectives are to provide an inexpensive to manufacture multipurpose vehicle system with interchangeable operational components and power supplies.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The invention will now be described, by way of example, with reference to the accompanying drawings, in which:

FIGS. 3A-3H illustrate perspective view of the vehicle system, showing multiple combinations of the rear operational modules attached to the body module, and showing a signal transmitted from a personal communication device to reconfigure the vehicle subsystems, in accordance with an embodiment of the present invention;

Like reference numerals refer to like parts throughout the various views of the drawings.

DETAILED DESCRIPTION OF THE INVENTION

Figure 1:
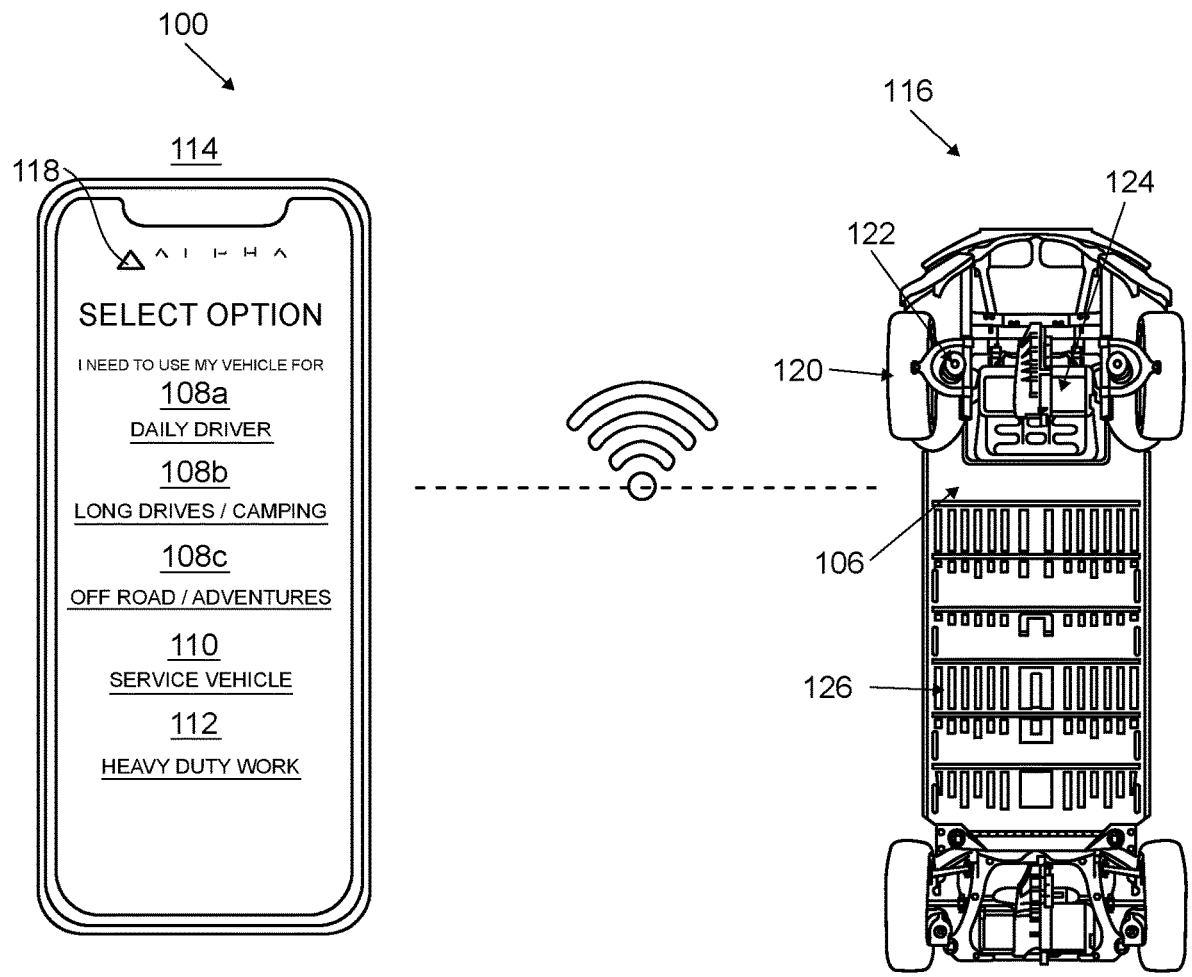
FIG. 1 illustrates a top view of an exemplary multipurpose electric vehicle control system, showing the software transmitting instructions to a control unit for reconfiguring the vehicle subsystems of an electric vehicle, in accordance with an embodiment of the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Specific dimensions and other physical characteristics relating to the embodiments disclosed herein are therefore not to be considered as limiting, unless the claims expressly state otherwise.

A multipurpose electric vehicle control system 100 is referenced in FIGS. 1-6. The multipurpose electric vehicle control system 100, hereafter "system 100" provides an electric vehicle 116. Those skilled in the art will recognize that the electric vehicle 116 utilizes electrical energy as a source of power. This electrical means can be a substitute for the vehicles using fossil fuels. The electric vehicle 116 can also be equipped with batteries having a large capacity in order to propel the electric vehicle 116 through large distances.

The electric vehicle 116 is made up of multiple detachably attached modules that can be interchanged to create different operational modes. The modules include: a chassis module 202, a body module 204, and one or more rear operational modules 206 (See FIG. 2). In one embodiment, the chassis module 202, the body module 204, and the one or more rear operational modules 206 are detachably attached to each other, enabling easy manipulation of the electric vehicle into different operational modes.

In addition to being comprised of detachable modules, the electric vehicle 116 has integrated therein, a control unit 106 and a machine-executable instruction 118, or software. The machine-executable instruction 118 provides instructions to a control unit 106 integrated into the electric vehicle 116, instructing to reconfigure the structural configuration of the vehicle subsystems. As FIG. 1 shows, this structural reconfiguration by the control unit 106 enables selective changes to the vehicle subsystems, which forms different operational modes for the electric vehicle 116.

In one non-limiting embodiment, the control unit 106 is configured to selectively switch vehicle subsystems from the electric vehicle 116, between a personal vehicle mode 108a-c, a fleet service vehicle mode 110, and a commercial vehicle mode 112. FIG. 1 illustrates an exemplary multipurpose electric vehicle control system 100, showing the software transmitting instructions to a control unit 106 for reconfiguring the vehicle subsystems of the electric vehicle 116. In one non-limiting embodiment, the personal vehicle mode comprises a daily driver mode 108a, a long drives/camping mode 108b, and a off road/adventures mode 108c. The fleet service vehicle mode may include a service vehicle mode 110. The commercial vehicle mode may include a heavy-duty work mode 112.

The control unit 106 is operable, and integrated, into an electric vehicle 116 that uses an electric motor subsystem 124 and a rechargeable battery subsystem 126 for propulsion. The machine-executable instructions 118 can be in the form of a downloadable software application, on a mobile communication device 114. The machine-executable instruction 118 transmits configuration instructions to the control unit 106 remotely. Further, as discussed above, the electric vehicle 116 is made up of multiple detachably attached modules that can be interchanged to create additional operational modes.

Consequently, the myriad combinations of operational modes for the electric vehicle 116 are determined by both, the control unit 106 that reconfigures the structural configuration of the vehicle subsystems, and the rearrangement of modules (the chassis module 202, the body module 204, and the one or more rear operational modules 206) that make up the electric vehicle 116.

Figure 2:
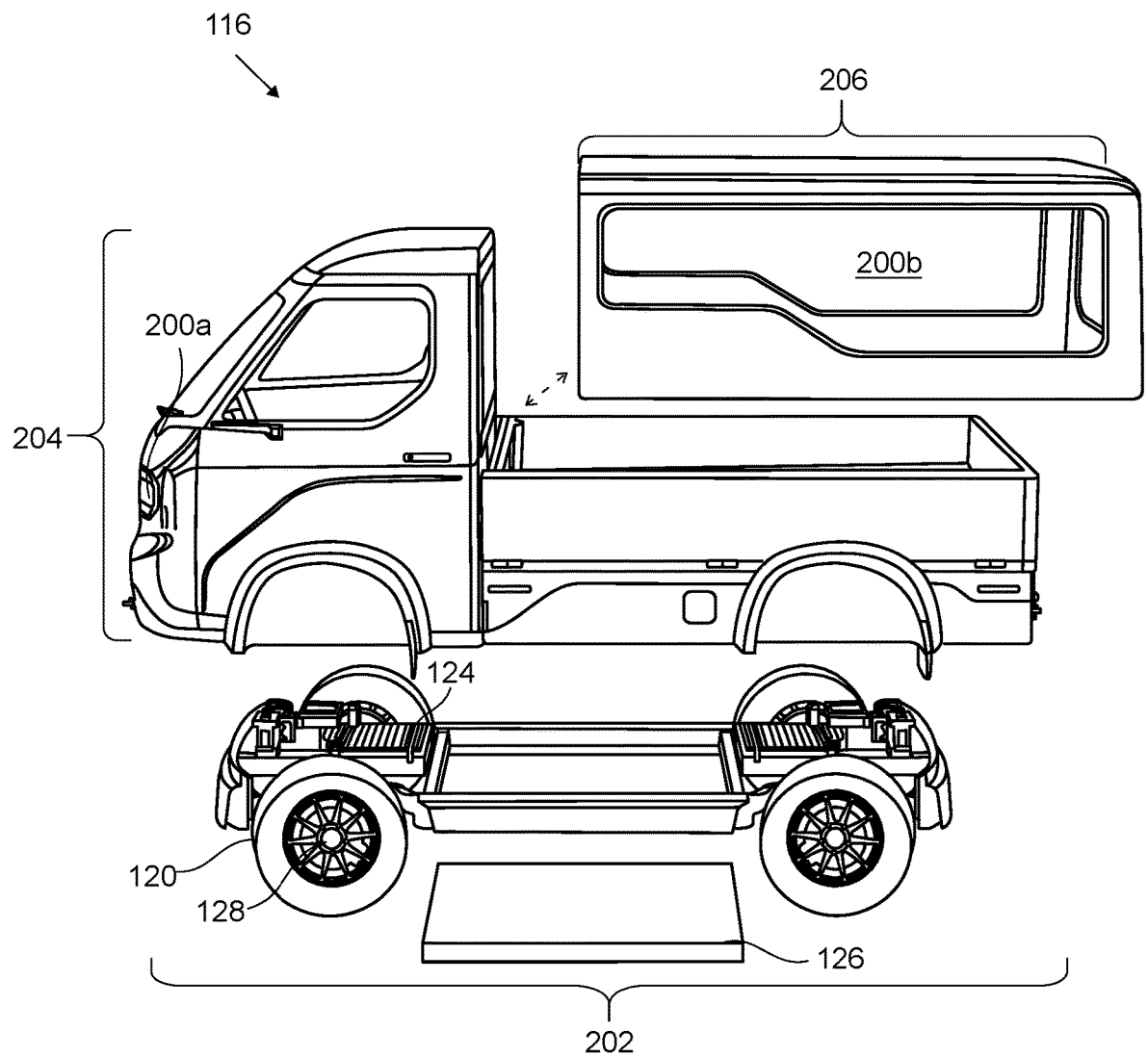
FIG. 2 illustrates a blow-up view of the multipurpose vehicle system, showing a chassis module, a body module, and a rear operational module, in accordance with an embodiment of the present invention.

As illustrated in FIG. 2, the electric vehicle 116 comprises a plurality of vehicle subsystems. The electric vehicle 116 comprises multiple vehicle subsystems that make up the necessary operational mechanisms for operating the electric vehicle 116. In one possible embodiment, the vehicle subsystems include, a wheel subsystem 120, a suspension subsystem 122, an electric motor subsystem 124, a rechargeable battery subsystem 126, a transmission subsystem 128, and an interchangeable panel subsystem 200a, 200b.

The vehicle subsystems can have their structure reconfigured, so as to be operable in a plurality of operational modes. In some embodiments, the operational modes may include, without limitation, a personal transport vehicle mode, a fleet service vehicle mode, and a commercial vehicle mode. In addition, vehicle related data for the fleet service vehicle mode and the commercial vehicle mode are managed by a software.

In addition to the vehicle subsystems, the electric vehicle 116 comprises three primary structural components: a chassis module 202, a body module 204, and one or more rear operational modules 206 (See FIG. 2). In one embodiment, the chassis module 202, the body module 204, and the one or more rear operational modules 206 are detachably attached to each other, enabling easy manipulation of the electric vehicle into different operational modes.

Specifically, the rear operation modules can be interchanged on the body module 204, so as to use a different kind of operational mode. For example, a first rear operational module has a van shell configuration, while a second rear operational module has a pickup truck bed configuration. The electric vehicle can thus, be converted from a van to a pickup truck by interchanging the first and second rear operational modules 206.

Looking now at FIGS. 3A-3G, any combination of an assortment of rear operational modules 102a-g attaches to the receiving dock at the rear end of the body module 204, such that multiple operational modes are formed. The rear operational modules are diverse in function and structure. In some embodiments, the rear operational modules 102a-c can be at least one of the following: a tractor body module 102a is shown in FIG. 3A; a van shell body module 102b is shown in FIG. 3B; a pickup truck body module 102c, which can carry a load, is shown in FIG. 3C.

Continuing with the exemplary operational modules that can interchangeably attach to the body module 204 of the electric vehicle 116, the rear operational modules 102d-g can include a tanker body module 102d, as shown in FIG. 3D; a delivery van shell body module 102e is shown in FIG. 3E; a dump truck body module 102f is shown in FIG. 3F; and a waste truck body module 102g is shown in FIG. 3G. Thus, by interchanging the rear operational modules 102a-g, different operational modes for the electric vehicle 116 can be achieved.

In addition to the reconfiguration of the rear operational modules 102a-g, the control unit 106 can also reconfigure the structural configuration of the vehicle subsystems. FIG. 3H shows a mobile communication device 114 transmitting signals to the control unit for additional reconfigurations to the vehicle subsystems. Thus, both the modules of the electric vehicle, and the vehicle subsystems can be reconfigured to achieve a desired vehicle operational mode.

As FIG. 2 shows, the chassis module 202 is a generally flat, rectangular, and rigid foundation. The chassis module 202 has a front end that orients towards a forward direction traveled by the vehicle system, and an opposing rear end. A pair of lateral sides extend between the front and rear ends of the chassis module 202. In one embodiment, a power supply compartment provides a secure location to detachably fasten a power source thereto. The power supply compartment may include a rectangular space that is sized and dimensioned to receive a fuel cell or a rechargeable battery.

Looking again at FIG. 1, the chassis module 202 supports the suspension subsystem 122. In some embodiments, the suspension devices may include, without limitation, struts, shock absorbers, and springs. The suspension subsystem 122 is adjustable to be harder or softer, depending on the required operational mode. For example, the personal transport vehicle mode may require a soft suspension subsystem 122, while a commercial vehicle mode, such as a truck, would require a more rigid vehicle suspension subsystem 122.

The chassis module 202 also carries the wheel subsystem 120 that is operatively connected to the suspension device. The wheel subsystem 120 can be at the corners of the chassis module 202, as illustrated in FIG. 1. In one possible embodiment, the wheel subsystem 120 comprises four wheels that are rotatable, so as to enable mobility of the chassis module 202. The wheel subsystem 120 may be rubber wheels, or may have a tire encompassing the wheels. As illustrated, there may be four wheels. However, in other embodiments, more or less than four wheels may be used.

The chassis module 202 may also include the electric motor subsystem 124 that is operatively connected to the wheel subsystem 120 for rotatably driving the wheel subsystem 120. In one embodiment, the electric motor subsystem 124 is operatively connected to the wheel subsystem 120. The electric motor subsystem 124 rotatably drives wheels, so as to generate motion of the chassis module 202.

The chassis module 202 also supports the rechargeable battery subsystem 126 that is operatively connected to the electric motor subsystem 124 for charging the electric motor subsystem 124. The rechargeable battery subsystem 126 provides electrical power, and is operatively connected to the electric motor subsystem 124. In one possible embodiment, the rechargeable battery subsystem 126 is configured to charge the electric motor subsystem 124 for driving the wheel subsystem 120.

Also, the rechargeable battery subsystem 126 provides electrical power to accessories and ancillary components of the electric vehicle 116. In one non-limiting embodiment, the rechargeable battery subsystem 126 is a lithium ion battery. However, in other embodiments, the rechargeable battery subsystem 126 utilizes different chemical elements and reactions therebetween to generate power.

The chassis module 202 also carries the transmission subsystem 128 that is operatively joined with the electric motor subsystem 124 and the wheel subsystem 120 for transmitting power from the electric motor subsystem 124 to the wheel subsystem 120. The reconfiguration of the transmission subsystem 128 can be useful in sport, winter, economy, and manual modes, in which the changes between gear ratios and other subsystem control parameters are modified so as to suit the driving conditions. In one non-limiting embodiment, the transmission subsystem 128 comprises a single-speed transmission. The single-speed is often sufficient because an electric vehicle provides sufficient torque, such that multiple are not required.

As discussed above, in addition to the chassis module 202, the electric vehicle 116 is also made up of a body module 204 that is detachably attachable to the chassis module 202. The body module 204 comprises an interchangeable panel subsystem 200a-b. The interchangeable panel subsystem 200a-b includes multiple panels that selectively display from different sections of the electric vehicle 116. For example, FIG. 2 shows a front panel 200a and a side panel 200b.

The control unit 106 serves to change the structural configuration of the panels in the panel subsystem 200a-b, so that the panels automatically replace each other, possibly through a slidable motion, in order to display. Thus, by changing the operational mode of the panel subsystem 200a-b with a personal communication device 114, the machine-executable instructions 118, or software, the panels can be interchanged.

Figure 4:
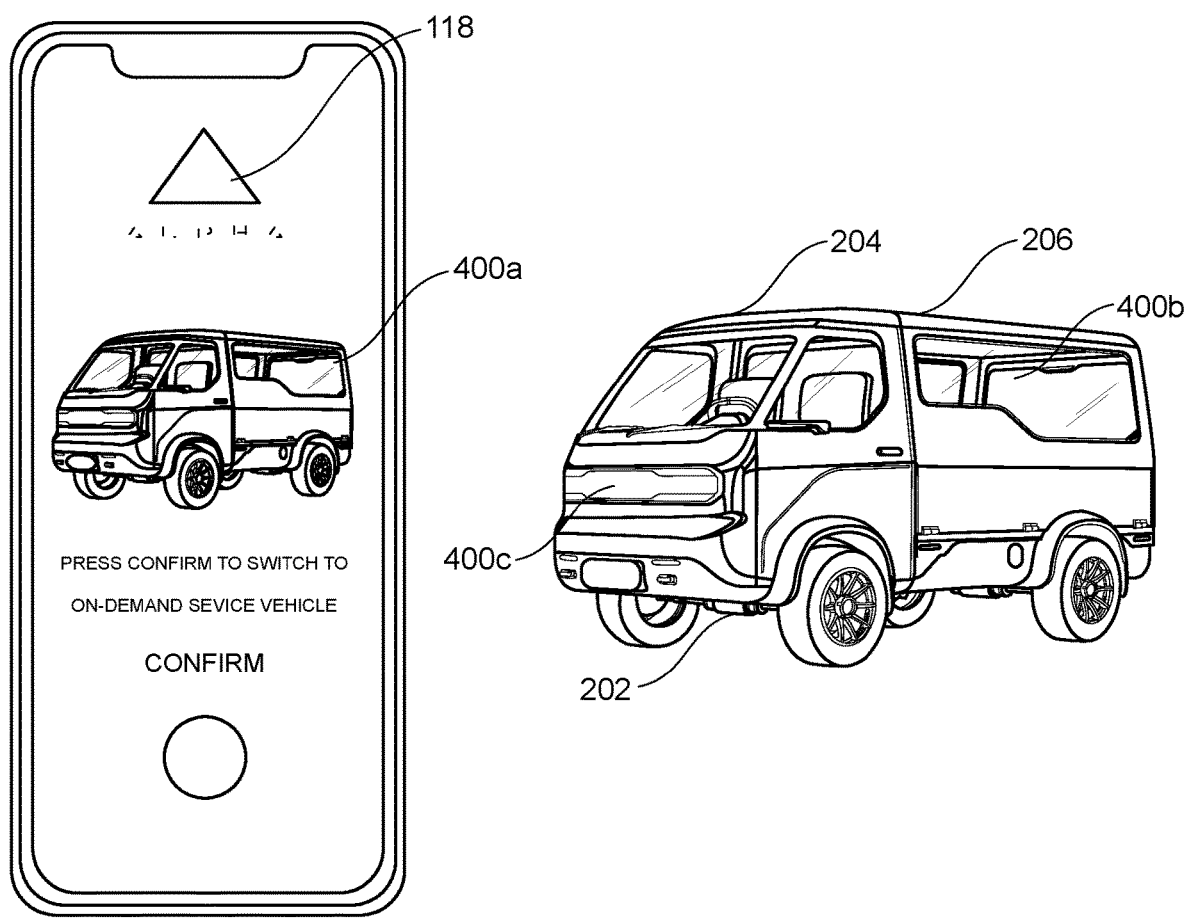
FIG. 4 illustrates a side view of an electrical vehicle showing a window panel being replaced by a sign panel, in accordance with an embodiment of the present invention.

As illustrated in FIG. 4, a window panel 400a is replaced by a sign panel 400b. The sign panel 400b slides over the window panel 400a to display a "Service Vehicle" signage. If the window panel 400a is desired, the personal communication device 114 transmits a signal to the control unit 106 to slidably move the sign panel 400. Additionally, a front panel 400c, comprising a headlight cutout, is shown at the front end of the electric vehicle 116. The control unit 106 could achieve the same reconfiguration of the front panel 1400c, sliding a differently shaped headlight cutout to give a new ornamental appearance to the front end of the electrical vehicle 116.

Looking back at FIG. 1, the electric vehicle 116 may also include one or more rear operational modules 206 that are interchangeably and detachably attached to the body module 204. Any combination of the rear operational modules 206 attaches to the body module 204. Thus, interchangeable rear operational modules 206 detachably and interchangeably attach to the rear end of the body module 204. The rear operational modules 206 create different operational modes for the vehicle system. Each operational mode enables the vehicle system to change its structural shape and purpose in the lifetime of the vehicle. Advantageously, as components are removed, replaced, or wear out over time, these used components can be recycled.

Thus, as described above, in addition to changing the vehicle subsystems with the control unit 106, interchanging different rear operation modules to the body module 204 serves to create different operational modes for the electric vehicle 116. For example, FIG. 5A references the rear operation module of the electric vehicle 116 is an all-purpose van 500*a*. This configuration can be used for rough terrain, moving items, and pulling a trailer. The control unit 106 also works to reconfigure the suspension subsystem 122*s* to be hard. In another example, shown in FIG. 5B, the rear operation module of the electric vehicle 116 is a delivery van shell 500*b*. This configuration can be used for storing and carrying large items, in a rural community.

Figure 5A:
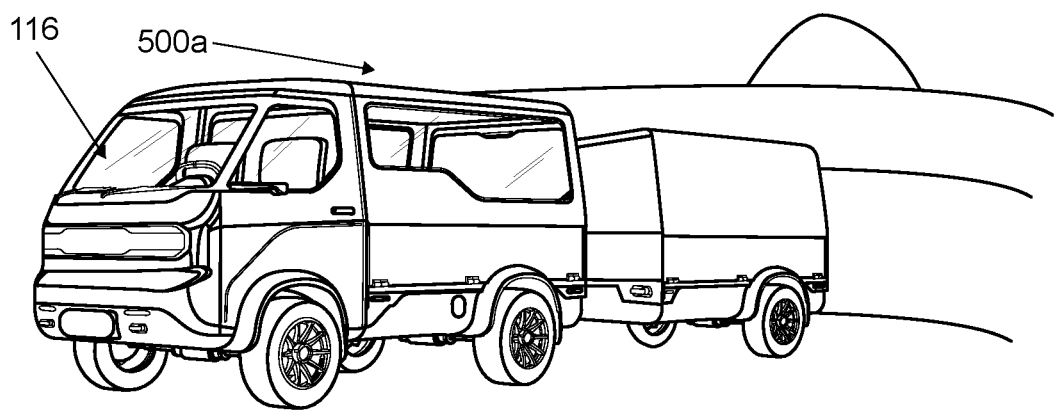
FIGS. 5A-5D illustrate views of multiple operational modes for the electric vehicle, in accordance with an embodiment of the present invention.
Figure 5B:
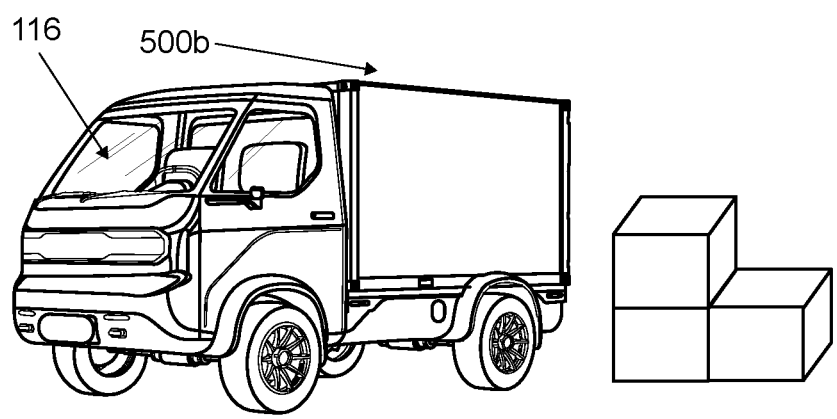
Figure 5C:
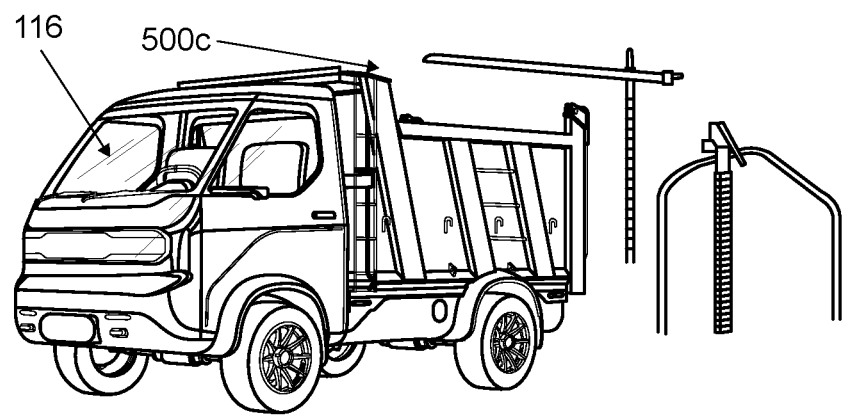
Figure 5D:
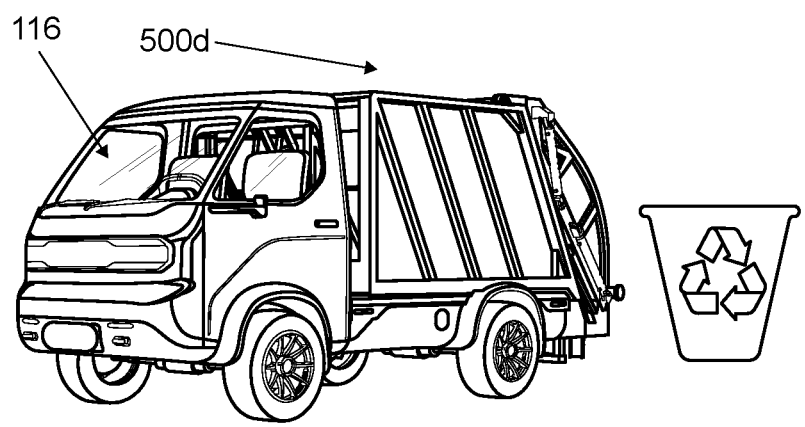

In another embodiment shown in FIG. 5C, the rear operation module is a dump truck bed 500*c*, and also includes a hydraulic jack that raises and lowers the bed for dumping the dirt and rubble therein. Thus, the electric vehicle 116 is in a dump truck operational mode, which can be reconfigured with the control unit 106 to increase power to the electric motor. Looking now at FIG. 5D, the rear operation module is a waste bin 500*d* for a waste recycle vehicle. The waste bin 500*d* collects municipal solid waste and transports it to a solid waste treatment facility, such as a landfill or transfer station.

As discussed above, the control unit 106 is also operable to reconfigure the structural configuration of the vehicle subsystems. The control unit 106, which is operatively connected to the vehicle subsystems, utilizes various sensors, links, transmitters, receivers, processors, and other control unit 106 mechanisms known in the art to change the configuration of the vehicle subsystems. For example, the control unit 106 can send a signal to the vehicle suspension subsystem 122 to increase or decrease resistance, i.e., become harder or softer. In response, a receiver and an electromechanical switch tighten or loosen a bracket around a spring that makes up the suspension subsystem 122.

In another example of the control unit 106 reconfiguring the structural configuration of the vehicle subsystems, the control unit 106 transmits a signal to an inverter or to the rechargeable battery subsystem 126, commanding that less power is used, which serves as a power management means. In response, the cable that carries the electric current is mechanically modified to adjust the amount of electricity running therethrough.

In yet another example, the control unit 106 transmits a signal to the wheel subsystem 120 to decrease the size of the wheels. A mechanical device at the rim of the wheels may then air to a predetermined psi. Thus, by changing the structural configuration of the vehicle subsystems, this causes the operational modes to be reconfigured to myriad operational types of vehicles.

The control unit 106 may operate by transmitting a signal to the vehicle subsystem commanding a reconfiguration. In some embodiments, the reconfigurations to the structural configuration of the vehicle subsystems may include, without limitation, performance settings, suspension adjustments, panel and window management, brake settings, transmission settings, security settings, battery management, power management, climate settings, entertainment settings.

These vehicle subsystems can be adjusted to a desired setting for driving in different environments and in different operational modes. For example, if a large commercial truck mode is required, the amount of power generated by the electric motor subsystem 124 is increased. In another example, if a fleet taxi vehicle mode is used, the electric motor subsystem 124 and the rechargeable battery subsystem 126 are reconfigured to draw less power, so as to increase the range of the rechargeable battery.

In some embodiments, the operational modes may include, without limitation, a personal transport vehicle mode 108*a*-*c*, a fleet service vehicle mode 110, and a commercial vehicle mode 112. The control unit 106 interchanges between modes by making changes to the vehicle subsystems, as commanded by a user. In some embodiments, the personal transport vehicle mode 108*a*-*c* may include a simple sedan, or economy car that is used by an individual for personal transport, such as coming and going to work, driving from the home to the store and back, and taking extended vacation road trips. Exemplary vehicle subsystem reconfigurations may include changing the suspension subsystem 122 to be softer, and changing the torque on the electric motor subsystem 124.

The fleet service vehicle mode 110 can include a sedan or a truck that is used for ferrying people and goods to and from different points. The fleet service vehicle mode may also include a fleet of commercial vehicles for a company, such as lease car from a Police Department, or delivery cars for a pizza delivery restaurant. The fleet service vehicle mode may also include the electric vehicle 116 serving as a taxi. Uber™, and other passenger services may be used in this manner. In some embodiments, the commercial vehicle mode 112 can include the electric vehicle 116 being reconfigured to carry heavy loads, such as when used as a dump truck. Exemplary changes to the vehicle subsystems may include increasing the power generated by the electric motor subsystem 124.

In some embodiments, the interchangeable panel subsystem 200 comprises one or more front panels detachably attached to a front end of the body module 204, and one or more rear panels detachably attached to a rear end of the body module 204. In some embodiments, the structural configuration of the front and rear panels is reconfigured when the front and rear panels are slidably urged to display from the front and rear ends of the body module 204.

In some embodiments, the interchangeable panel subsystem 200 comprises one or more side panels detachably attached to a left side and a right side of the body module 204, and one or more roof panels detachably attached to a top end of the body module 204. The structural configuration of the side panels is reconfigured when the side panels are slidably urged to display from the left and right sides of the body module 204. The structural configuration of the suspension subsystem 122 is reconfigured when the suspension subsystem 122 is adjusted to be softer or harder.

In one embodiment, the interchangeable panel subsystem 200 comprises one or more front panels that detachably attach to the front end of the body module 204. In another embodiment, one or more rear panels detachably attach to the rear end of the body module 204. In some embodiments, the front and rear panels are operational to illuminate. However, a lighting system may be built into the body module 204 or the chassis module 202.

In yet another embodiment, the front panel have openings that allow the light to pass through. The shape and design of the openings in the front and rear panels can be different and interchanged, so as to provide different lighting effects. Furthermore, the panels may have indicia, coloring, patterns, and texture that provides a different visual for the system. For example, a sign indicating large loads or advertising can be printed onto the front and rear panels.

In another example of reconfiguration, the structural configuration, the rechargeable battery subsystem 126 is reconfigured when the rechargeable battery or cables thereof are reconfigured to generate more or less electrical charge for charging the electric motor subsystem 124. Additionally, the structural configuration of the transmission subsystem 128 is reconfigured when the transmission subsystem 128 increases or decreases the number of gears available for transmitting power from the electric motor subsystem 124 to the wheel subsystem 120. This can work to vary the torque being offered to the wheel subsystem 120.

The system 100 also includes a machine-readable storage medium containing machine-executable instructions 118. The machine-executable instructions 118 may be software that is designed to instruct the control unit 106 on reconfigurations, and also to manage vehicle-related data. In one embodiment, the machine-executable instructions 118 are operable to instruct the control unit 106 to reconfigure the structural configuration of the vehicle subsystems, so as to achieve a desired vehicle operational mode. The machine-executable instructions 118 may be operable and in communication with various sensors, linkages, motors, and electromechanical devices in the vehicle subsystems.

The machine-executable instructions 118 are also configured to manage vehicle-related data. In one non-limiting embodiment, the machine-executable instructions 118 include database software, accounting software, and calendar software. In some embodiments, the vehicle-related data management may include, without limitation, a vehicle insurance, a vehicle maintenance schedule, and a vehicle service log. This can be useful when operating the vehicle in the fleet service vehicle mode. The miles driven can be recorded and stored for future billing. Also, a company can better organize maintenance schedules for a large fleet of vehicles when the software determines the maintenance period for each vehicle. Furthermore, it can be useful to be reminded by the software that the insurance payment is due at a certain date.

In some embodiments, the machine-executable instructions 118 operate remotely from a mobile communication device 114. In this manner, a user, such as the vehicle operator, can change the operational mode of the vehicle at any time to achieve a desired operational mode. For example, the vehicle operator can drive the vehicle in the personal transport vehicle mode for shopping, or going to a normal office job. However, in the evening or on weekends, the vehicle operator can indicate to the control unit 106, through the software app on a personal communication device 114, to change, or structurally reconfigure, the electric vehicle 116 to a fleet service vehicle mode. After changing the operational mode, the vehicle operator may then drive the electric vehicle 116 as a taxi, or Uber™.

Figure 6:
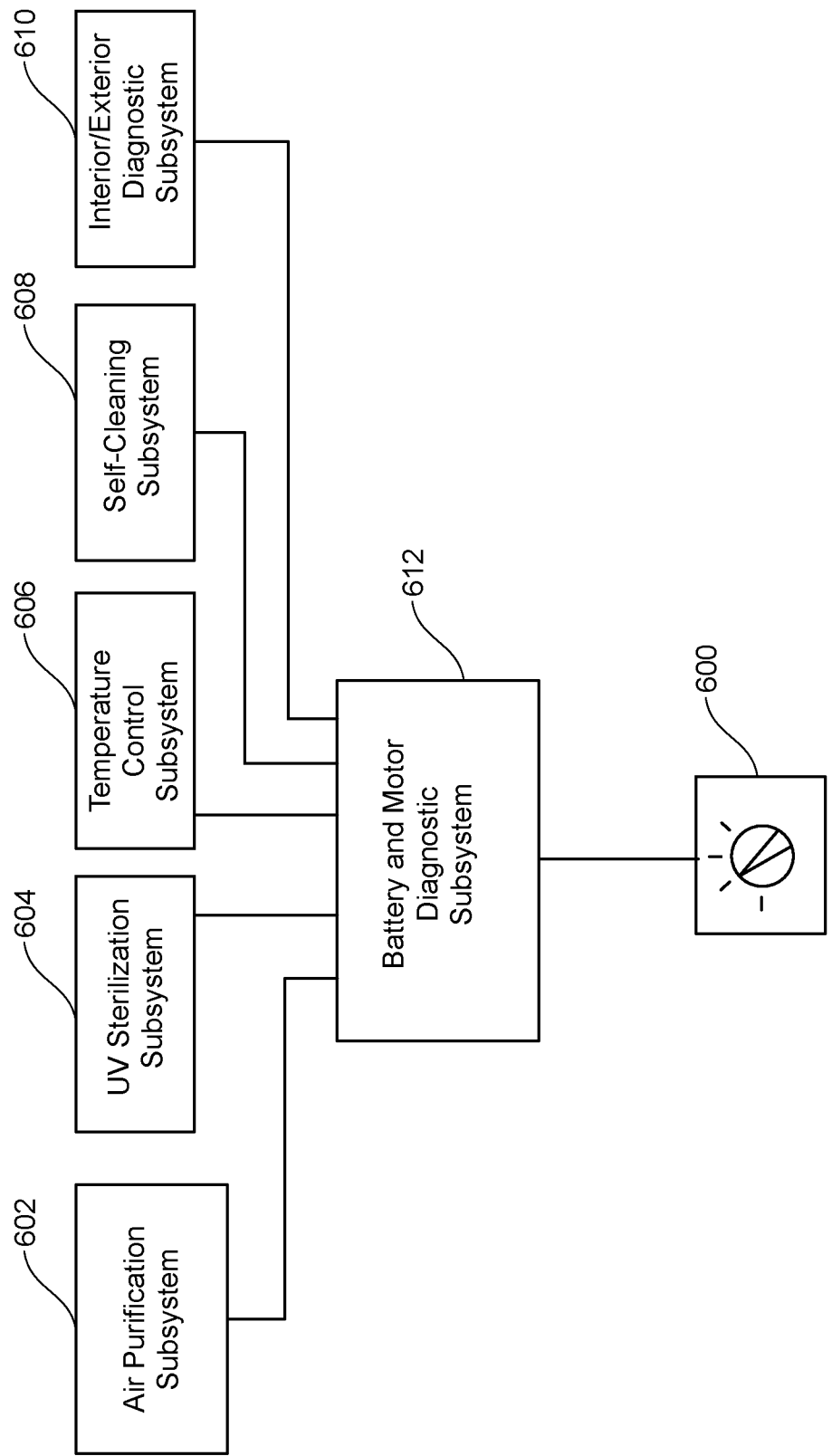
FIG. 6 illustrates an exemplary vehicle control system having multiple control subsystems, in accordance with an embodiment of the present invention.

FIG. 6 illustrates an exemplary vehicle control system 600 that has multiple control subsystems to control different functions of the electric vehicle. In one embodiment, the control system 600 includes an air purification subsystem 602 that filters out harmful particles form the ventilation in the vehicle. This can include air filters. The control system 600 also includes sterilization of the interior of the vehicle through UV interior lighting subsystem 604. This can include a disinfection method that uses short-wavelength ultraviolet light to kill or inactivate microorganisms.

In some embodiments, the control system 600 also includes a temperature control subsystem 606, which can include a heater, an air conditioner, and a defroster. In another embodiment, the control system 600 also includes a self-cleaning subsystem 608. Additionally, the control system 600 may also comprise an interior and exterior diagnostic subsystem 610 that indicates exterior and interior components that require replacement. For example, the exterior brake lights need replacement after 1000 hours of use. In some embodiments, the control system 600 also includes a battery and motor diagnostic subsystem 612 that indicates battery and motor components that require replacement. For example, a battery replacement light indicates the battery is losing charge.

In conclusion, the system 100 provides an electric vehicle 116 made up of multiple detachably attached modules that can be interchanged to create different operational modes. The system also includes a control unit 106 and a software that direct reconfigurations to vehicle subsystems, so as to selectively create different operational modes. The software also manages vehicle-related data. The structural configuration of vehicle subsystems may include: performance settings, suspension adjustments, panel management, brake settings, transmission settings, security settings, battery management, power management, and entertainment settings. By making these reconfigurations to vehicle subsystems the electric vehicle selectively operates between a personal transport vehicle mode, a fleet service vehicle mode, and a commercial vehicle mode. The software also manages vehicle-related data, including: vehicle insurance, vehicle maintenance schedule, and vehicle service logs. A personal communication device, such as a smart phone, can control the software through a software application.

These and other advantages of the invention will be further understood and appreciated by those skilled in the art by reference to the following written specification, claims and appended drawings.

Because many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A multipurpose electric vehicle control system, comprises:
   an electric vehicle comprising a plurality of vehicle subsystems, the vehicle subsystems being operable in a plurality of operational modes, the vehicle subsystems including:
      a chassis module having a suspension subsystem, a wheel subsystem operatively connected to the suspension device, an electric motor subsystem operatively connected to the wheel subsystem for rotatably driving the wheel subsystem, a rechargeable battery subsystem operatively connected to the electric motor subsystem for charging the electric motor subsystem, and a transmission subsystem operatively joined with the electric motor subsystem and the wheel subsystem for transmitting power from the electric motor subsystem to the wheel subsystem;
      a body module being detachably attachable to the chassis module, the body module comprising an interchangeable panel subsystem; and
      one or more rear operational modules being interchangeably and detachably attached to the body module, whereby any combination of the rear operational modules attaches to the body module; and
   a control unit operable to reconfigure a structural configuration of the vehicle subsystems, whereby changing the structural configuration of the vehicle subsystems causes the operational modes to be reconfigured, wherein the structural configuration of the interchangeable panel system is reconfigured when multiple panels are slidably urged to display from the body module.

2. The system of claim 1, further comprising a machine-readable storage medium containing machine-executable instructions operable to instruct the control unit to reconfigure the structural configuration of the vehicle subsystems, the machine-executable instructions further being operable to manage vehicle-related data.

3. The system of claim 2, wherein the machine-executable instructions operate remotely from a mobile communication device.

4. The system of claim 1, wherein the operational modes comprise a personal transport vehicle mode, a fleet service vehicle mode, and a commercial vehicle mode.

5. The system of claim 1, wherein the reconfigurations to the structural configuration of the vehicle subsystems include, at least one of the following: performance settings, suspension adjustments, panel and window management, brake settings, transmission settings, security settings, battery management, power management, climate settings, entertainment settings.

6. The system of claim 2, wherein the vehicle-related data management includes at least one of the following: a vehicle insurance, a vehicle maintenance schedule, and a vehicle service log.

7. The system of claim 1, wherein the interchangeable panel subsystem comprises one or more front panels detachably attached to a front end of the body module, and one or more rear panels detachably attached to a rear end of the body module.

8. The system of claim 7, wherein the structural configuration of the front and rear panels is reconfigured when the front and rear panels are slidably urged to display from the front and rear ends of the body module.

9. The system of claim 1, wherein the interchangeable panel subsystem comprises one or more side panels detachably attached to a left side and a right side of the body module, and one or more roof panels detachably attached to a top end of the body module.

10. The system of claim 9, wherein the structural configuration of the side panels is reconfigured when the side panels are slidably urged to display from the left and right sides of the body module.

11. The system of claim 1, wherein the structural configuration of the suspension subsystem is reconfigured when the suspension subsystem is adjusted to be softer or harder.

12. The system of claim 1, wherein the structural configuration of the rechargeable battery subsystem is reconfigured when the rechargeable battery subsystem is adjusted to generate more or less electrical charge for charging the electric motor subsystem.

13. The system of claim 1, wherein the structural configuration of the transmission subsystem is reconfigured when the transmission subsystem increases or decreases the number of gears available for transmitting power from the electric motor subsystem to the wheel subsystem.

14. The system of claim 1, further comprising an air purification subsystem, a UV interior lighting subsystem, a temperature control subsystem, a self-cleaning subsystem an interior and exterior diagnostic subsystem, and a battery and motor diagnostic subsystem.

15. A multipurpose electric vehicle control system, comprises:

an electric vehicle comprising a plurality of vehicle subsystems, the vehicle subsystems being operable in a plurality of operational modes, the operational modes comprising a personal transport vehicle mode, a fleet service vehicle mode, and a commercial vehicle mode, the vehicle subsystems including:

a chassis module having a suspension subsystem, a wheel subsystem operatively connected to the suspension device, an electric motor subsystem operatively connected to the wheel subsystem for rotatably driving the wheel subsystem, a rechargeable battery subsystem operatively connected to the electric motor subsystem for charging the electric motor subsystem, and a transmission subsystem operatively joined with the electric motor subsystem and the wheel subsystem for transmitting power from the electric motor subsystem to the wheel subsystem;

a body module being detachably attachable to the chassis module, the body module comprising an interchangeable panel subsystem; and one or more rear operational modules being interchangeably and detachably attached to the body module, whereby any combination of the rear operational modules attaches to the body module;

a control unit comprising a processor, the control unit operable to reconfigure a structural configuration of the vehicle subsystems, whereby changing the structural configuration of the vehicle subsystems causes the operational modes to be reconfigured, wherein the structural configuration of the interchangeable panel subsystem is reconfigured when multiples panels are slidably urged to display from the body module; and a machine-readable storage medium containing machine-executable instructions operable to instruct the control unit to reconfigure the structural configuration of the vehicle subsystems, the machine-executable instructions further being operable to manage vehicle-related data.

16. The system of claim 15, wherein the reconfigurations to the structural configuration of the vehicle subsystems include, at least one of the following: performance settings, suspension adjustments, panel and window management, brake settings, transmission settings, security settings, battery management, power management, climate settings, entertainment settings.

17. The system of claim 15, wherein the vehicle-related data management includes at least one of the following: a vehicle insurance, a vehicle maintenance schedule, and a vehicle service log.

18. The system of claim 15, wherein the structural configuration of the suspension subsystem is reconfigured when the suspension subsystem is adjusted to be softer or harder.

19. A multipurpose electric vehicle control system, comprises:

an electric vehicle comprising a plurality of vehicle subsystems, the vehicle subsystems being operable in a plurality of operational modes, the operational modes comprising a personal transport vehicle mode, a fleet service vehicle mode, and a commercial vehicle mode, the vehicle subsystems including:

a chassis module having a suspension subsystem, a wheel subsystem operatively connected to the suspension device, an electric motor subsystem operatively connected to the wheel subsystem for rotatably driving the wheel subsystem, a rechargeable battery subsystem operatively connected to the electric motor subsystem for charging the electric motor subsystem, and a transmission subsystem operatively joined with the electric motor subsystem and the wheel subsystem for transmitting power from the electric motor subsystem to the wheel subsystem;

a body module being detachably attachable to the chassis module, the body module comprising an interchangeable panel subsystem; and one or more rear operational modules being interchangeably and detachably attached to the body module, whereby any combination of the rear operational modules attaches to the body module;

a control unit comprising a processor, the control unit operable to reconfigure a structural configuration of the vehicle subsystems, whereby changing the structural configuration of the vehicle subsystems causes the operational modes to be reconfigured, whereby the structural configuration of the interchangeable panel subsystem is reconfigured when multiples panels are slidably urged to display from the body module, whereby the structural configuration of the suspension subsystem is reconfigured when the suspension subsystem is adjusted to be softer or harder, whereby the structural configuration of the rechargeable battery subsystem is reconfigured when the rechargeable battery subsystem is adjusted to generate more or less electrical charge, whereby the structural configuration of the rechargeable battery subsystem is reconfigured when the rechargeable battery subsystem is adjusted to generate more or less electrical charge for charging the electric motor subsystem, whereby the structural configuration of the electric motor subsystem is reconfigured when the electric motor subsystem is adjusted to increase or decrease power; and a machine-readable storage medium containing machine-executable instructions operable to instruct the control unit to reconfigure the structural configuration of the vehicle subsystems, the machine-executable instructions further being operable to manage vehicle-related data.

* * * * *